United States Patent [19]

Stafford

[11] Patent Number: 5,504,575
[45] Date of Patent: Apr. 2, 1996

[54] SLM SPECTROMETER

[75] Inventor: Ronald E. Stafford, Wylie, Tex.

[73] Assignee: Texas Instruments Incorporated, Dallas, Tex.

[21] Appl. No.: 79,691

[22] Filed: Jun. 17, 1993

Related U.S. Application Data

[63] Continuation of Ser. No. 812,508, Dec. 20, 1991, abandoned.

[51] Int. Cl.⁶ ........................................................ G01J 3/28
[52] U.S. Cl. ............................................ 356/330; 356/328
[58] Field of Search ..................................... 356/326, 328, 356/330; 359/291, 292

[56] References Cited

U.S. PATENT DOCUMENTS

| | | | |
|---|---|---|---|
| 2,721,259 | 10/1955 | Krasno . | |
| 4,193,691 | 3/1980 | Fjarlie | 356/330 |
| 4,448,529 | 5/1984 | Krause | 356/310 |
| 4,743,112 | 5/1988 | Burke | 356/326 |
| 4,760,258 | 7/1988 | Gast et al. | 250/347 |
| 4,790,654 | 12/1988 | Clarke | 356/310 |
| 4,799,795 | 1/1989 | Fateley | 356/330 |
| 4,810,092 | 3/1989 | Auth | 356/346 |
| 4,930,865 | 6/1990 | Dosmann | 356/326 |
| 4,969,740 | 11/1990 | Sonobe | 356/326 |
| 4,983,039 | 1/1991 | Harada et al. | 356/328 |
| 5,037,173 | 8/1991 | Sampsell et al. | 385/17 |
| 5,061,049 | 10/1991 | Hornbeck | 359/224 |
| 5,090,807 | 2/1992 | Tai | 356/330 |

FOREIGN PATENT DOCUMENTS

| | | | |
|---|---|---|---|
| 0075171A1 | 3/1983 | European Pat. Off. | G01J 3/32 |
| 0454124A1 | 10/1991 | European Pat. Off. | G01J 3/44 |

OTHER PUBLICATIONS

Treado, et al.; "A Thousand Points of Light: The Hadamard Transform in Chemical Analysis and Instrumentation", Analytical Chemistry, vol. 61, No. 11, Jun. 1, 1989, pp. 723A–734A.

Primary Examiner—Vincent P. McGraw
Assistant Examiner—K. P. Hantis
Attorney, Agent, or Firm—Charles A. Brill; James C. Kesterson; Richard L. Donaldson

[57] ABSTRACT

A SLM spectrometer is provided that employs an entrance slit or a collimator to provide parallel rays of radiation to a prism which disperses the incident radiation into an associated wavelength spectrum. The resulting spectrum from the prism is incident upon a spatial light modulator (SLM), such as a deformable mirror device (DMD). By selectively activating (or deactivating) a small portion of the surface of the SLM, i.e. a cell on the SLM, it is possible to selectively reflect or transmit a portion of the spectrum incident upon the SLM onto a focusing device, such as a parabolic focusing mirror. The focusing device in turn focuses the portion of the spectrum reflected by the selected cells on the SLM to a sensor. The wavelength selected is a function of which row of cells are activated (or deactivated) in the SLM. The SLM spectrometer of the present invention may be used to analyze visible light and light that is near visible, such as the near infrared or ultraviolet regions. The output of the sensor or detector may be appropriately amplified and after appropriate calibration employed to determine the amount of energy in a particular wavelength or band of wavelengths.

12 Claims, 2 Drawing Sheets 5,504,575

SLM SPECTROMETER

This application is a continuation of application Ser. No. 07/812,508, filed Dec. 20, 1991, now abandoned.

BACKGROUND OF THE INVENTION

This invention relates to spectrometers, and more particularly, relates to spectrometers employing a spatial light modulator (SLM), such as a deformable mirror device (DMD).

Spectrometers function using the principle of dispersion of light which occurs when rays of light are deviated, typically by a diffraction grating or refracted through a prism. Diffraction gratings behave optically like a multiplicity of very narrow individual slits which cause light rays to be deviated at angles depending upon the wavelength of those rays. Prisms cause dispersion of light since the angle of deviation of a light ray as it passes through a prism is a function of its wavelength; this wavelength dependent angular deviation is due to the fact that optical materials exhibit differing indexes of refraction for differing wavelengths. Spectrometer systems using a prism as a dispersing element have inherent advantages over those using a diffraction grating-type dispersion element since they are more efficient in terms of light transmission and less troubled by any stray light. Accordingly, many existing designs of spectrometers employ prism-type dispersion elements.

In existing spectrometers, light transmitted through a slit is dispersed using a diffraction grating or prism. The dispersed light is then imaged onto a detection focal plane, which typically contains an array of minute photosensitive elements. Most spectrometers include a collimator to make all the light rays incident on the grating or prism parallel. Collimation is necessary to control aberrations which result when non-collimated light is transmitted through the dispersing element. However, current spectrometers are relatively bulky instruments since the optical ray paths tend to be fairly long. In addition, current spectrometers require mechanical motion and rotate the dispersing element to scan wavelengths past the detectors. These mechanical motions cause vibrations and result in wear, which may cause alignment and/or calibration problems.

These and other limitations and disadvantages of the prior art are overcome by the present invention, however, and an SLM spectrometer is provided for measuring the amount of energy associated with various wavelengths in a spectrum.

SUMMARY OF THE INVENTION

In a preferred embodiment of the present invention, an SLM spectrometer is provided. More particularly, the spectrometer of the present invention employs an entrance slit and/or a collimator to provide parallel rays of radiation to a prism, grating, or any other type of wavelength dispersing element which disperses the radiation incident thereon into a spectrum of wavelengths of various orders. A spectrum resulting from the preferred prism (or other dispersing element) is made to be incident upon a spatial light modulator (SLM), such as a deformable mirror device (DMD), a magnetooptic modulator, or a liquid crystal device (LCD). By selectively activating a small portion of the SLM, it is possible to selectively reflect or transmit a portion of the spectrum incident upon the SLM to a focusing device, which is preferably a parabolic focusing mirror; other types of focusing devices, such as another type of mirror, a lens or lens system may be employed. The focusing device in turn focuses the portion of the spectrum reflected or transmitted by the activated portion of the SLM surface to a sensor or detector. Alternatively, the focusing device may focus the portion of the spectrum reflected or transmitted by a deactivated portion of the SLM surface to a sensor or detector. Also, for some embodiments, the SLM and focusing device may be combined into one device.

The SLM spectrometer of the present invention may be used to analyze visible light and light that is near visible, such as the near infrared or ultraviolet regions. The output of the sensor or detector may be appropriately amplified and, after appropriate calibration (using a known wavelength of known intensity), employed to determine the amount of energy in a particular wavelength, or band of wavelengths. The particular wavelength (or band of wavelengths) measured by the detector is a function of the wavelengths in the spectrum from the preferred prism dispersing element that are incident upon the surface area "activated" (or "deactivated") in the SLM. In this manner, the SLM spectrometer of the present invention eliminates the overall mechanical motion required of conventional spectrometers employing either rotating prisms or rotating gratings, i.e. those that must rotate the prism or grating to select the wavelength(s) measured by the detector.

It is an object of the present invention to provide an SLM spectrometer.

It is an object of the present invention to provide a spectrometer that does not require overall mechanical motion of the radiation dispersing elements once the dispersing elements are fixed relative to the radiation paths.

Accordingly, these and other objects and advantages of the present invention will become apparent from the following detailed description, wherein reference is made to the figures in the accompanying drawings.

IN THE DRAWINGS

DETAILED DESCRIPTION

Figure 1:
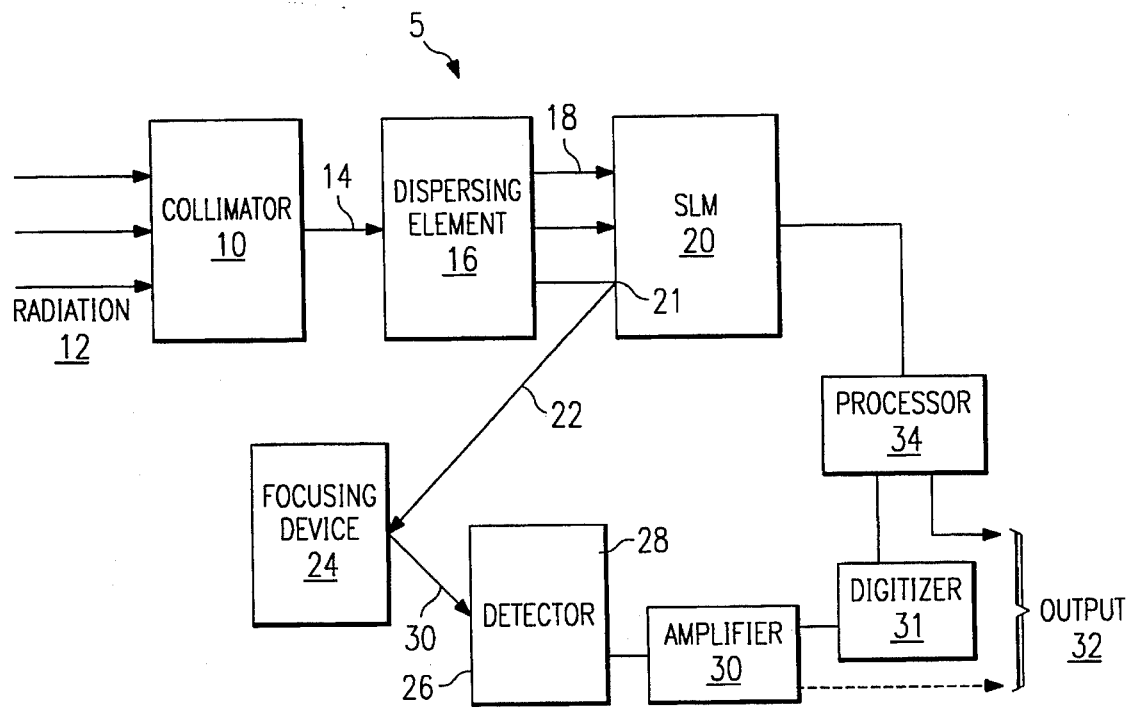
FIG. 1 depicts a functional block diagram of components of an SLM spectrometer of the present invention.

Referring now to FIG. 1, there may be seen a simplified functional block diagram of components of an SLM spectrometer 5 of the present invention. More particularly, there may be seen a collimator 10 that renders radiation 12 to be analyzed into a parallel beam 14 that falls upon a dispersing element 16. The dispersing element 16 disperses the parallel beam 14 into a dispersed, linear wavelength spectrum 18 of various orders. Preferably, an order is selected for analysis that does not overlap with any other orders. The higher the order, the more dispersed the spectrum becomes. A spatial light modulator (SLM) 20 is positioned to receive at least a portion of the selected order of wavelength spectrum on its active surface 21. Although depicted as a reflective type SLM, the SLM 20 may be a transmissive or reflective type of device. The SLM 20 contains an array of cells on its active surface 21 that may be selectively and individually activated. The array maybe a linear or area array, and the cells on SLM 20 may be very small. The SLM of the present invention may be, for example, but not limited to, a deformable mirror device (DMD), a liquid crystal device (LCD), or a magneto-optic modulator, and may employ a linear or aerial array of such types of devices. As previously mentioned, focusing device 24 is preferably a parabolic focusing mirror, but might be another type of mirror or a lens or lens system.

The activated cell (or cells) of the SLM 20 transmit or reflect 22 that portion of the wavelength spectrum 18 incident thereon. Alternatively, a deactivated cell (or cells) of the SLM 20 transmit or reflect 22 that portion of the wavelength spectrum 18 incident thereon. This selected portion of wavelength 22 is then focused by a focusing device 24 onto a focal plane 26. A detector 28 is positioned at the focal plane 26 and receives the selected radiation 30. Once aligned for these paths of the radiation beams in this manner, these components may be locked into these positions.

The signal from the detector 28 may be appropriately amplified by an amplifier 30 and provided as an output 32, or preferably provided as an input to a processor (which may be a microprocessor) 34. This processor 34 in turn may control or select which cells of the SLM are activated (or deactivated) and accordingly may combine the selected wavelength with the detected signal to provide an intensity versus wavelength spectrum as an output 32. The processor preferably contains appropriate software to,control the SLM and make selected outputs. The processor 32 may also contain software for analyzing and/or adjusting the signals from the detector.

Figure 2:
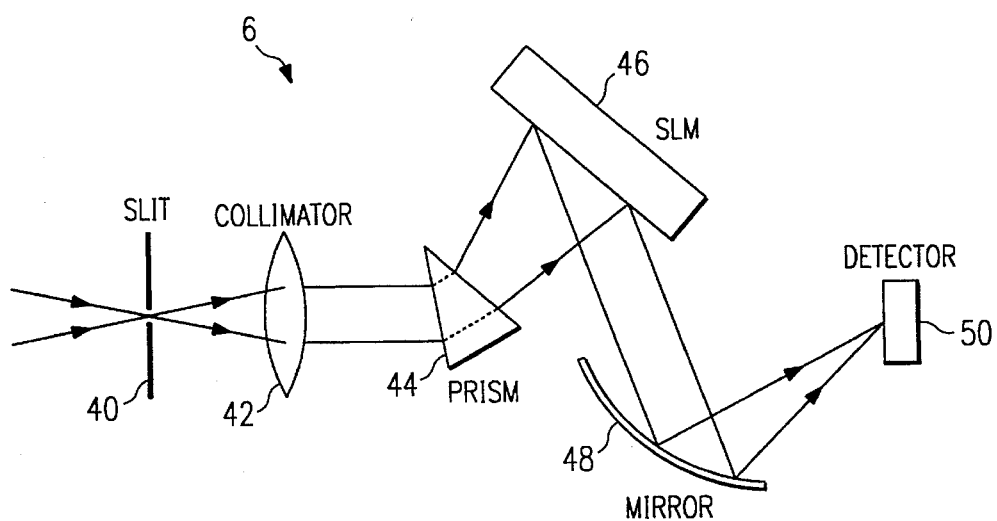
FIG. 2 depicts a general arrangement of components of an SLM spectrometer of the present invention.

Referring now to FIG. 2, it may be seen that one embodiment of the SLM spectrometer of the present invention preferably employs an entrance slit 40 followed by an appropriate collimation lens, or lens system, 42 to ensure that the rays of radiation to be analyzed that are passing through to the dispersing element 44 are converted to parallel beams prior to incidence upon the dispersing element 44. Although both a slit 40 and collimator 42 are depicted in FIG. 2, either one may be employed without the other.

In addition, it may be seen that an SLM spectrometer 6 of the present invention preferably employs a conventional prism as its dispersing element 44 to disperse the incident parallel radiation beam into a dispersed, linear wavelength spectrum of various orders, where wavelength is determined by position within the linear range of the spectrum output from the prism. In addition, the dispensing power of the prism may be selected based upon the intended use of the spectrometer of the present invention. More particularly, when higher resolution is needed, a prism of higher indices of refraction may be employed and the spacing between the prism and SLM 46 increased to provide a physically increased wavelength spectrum at the SLM 46, and/or a higher order may be employed. Also several SLM's may be appropriately arranged and employed as an "extended" SLM for such increased wavelength spectrums. Other dispersing means 44 may be employed, such as for example, but not limited to a reflection or transmission grating. The dispersed wavelength spectrum from the prism is made to fall upon a spatial light modulator (SLM) 46, which is preferably a deformable mirror device (DMD).

A DMD may consist of a linear or aerial array of micromirrors that may be selectively activated to rotate to preselected angles. U.S. Pat. No. 5,061,049, issued Oct. 29, 1991, and assigned to Texas Instruments Incorporated describes some examples of DMD's, such as the torsion beam DMD, and is incorporated herein by reference. Generally, torsion beam DMD devices may have a no applied voltage, or resting state, and either a positive or negative angle or deflection resulting from the application of a voltage. The direction of the deflection is determined by which address electrode the voltage is applied to. Other DMD mirrors may be such that the selected mirror (or mirrors) may be positioned at a variable and preselected angle based upon the application of a variable and preselected voltage to the mirror. Other types of SLM 46 devices may be employed instead of a DMD in the SLM spectrometer 6 of the present invention.

The SLM spectrometer of the present invention may be used to analyze visible light and light that is near visible, such as the near infrared or ultraviolet regions. The output of the sensor or detector may be appropriately amplified and, after appropriate calibration (using a known wavelength of known intensity), employed to determine the amount of energy in a particular wavelength, or band of wavelengths. The particular wavelength (or band of wavelengths) measured by the detector is a function of the wavelengths in the spectrum from the preferred prism dispersing element that are incident upon the surface area "activated" (or "deactivated") in the SLM. In this manner, the SLM spectrometer of the present invention eliminates the overall mechanical motion required of conventional spectrometers employing either rotating prisms or rotating gratings, i.e. those that must rotate the prism or grating to select the wavelength(s) measured by the detector.

Figure 3:
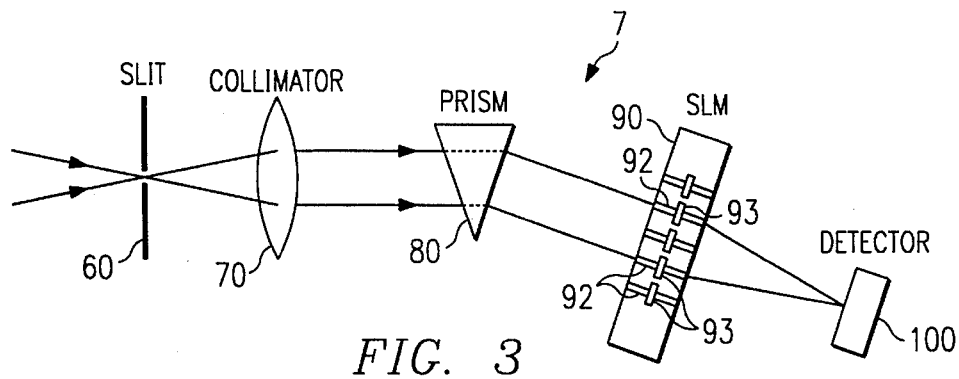
FIG. 3 depicts an alternative general arrangement of components of an SLM spectrometer of the present invention.

Referring now to FIG. 3, another type of SLM 90 employed in the SLM spectrometer 7 of the present invention may be a linear array of small optical fibers 92 (arranged side-by-side) disposed to receive the dispersed spectrum into one end (inlet) and pass their respective discrete portions of the spectrum out at the other end (outlet) to a detector 100. In addition, each optical fiber contains an optical shutter (or switch) 93 between the inlet and outlet ends. The optical shutters or switches 93 are normally closed to block any radiation in their respective optical fiber 92 from the detector 100, and are selectively opened to analyze the spectrum incident on the array of fibers. After the optical shutters 93, the optical fibers are twisted and aligned to focus their respective output radiation onto the detector 100. An array of small liquid crystal devices (LCDs) may be positioned in a parallel set of openings in the array of fibers and may be employed as the optical shutters. The absorption wavelength(s) of the type of optical fiber employed must be outside the wavelengths of the spectra of interest. For this embodiment, the SLM and focusing device of FIG. 1 are combined into one device.

The spacing between the SLM 90 and the prism 80 is a function of the amount of dispersion of the prism (dispersion power) and the extent of the active surface of the SLM, such as the size of the array of mirrors on a DMD device. More particularly, the spacing should be such that the total spectrum of wavelengths desired to be analyzed exiting from the prism falls upon the active surface (or surfaces) of the SLM device (or devices). As noted hereinbefore, a plurality of SLM's may be configured as an "extended" SLM and employed to provide for increased resolution. A typical size of a DMD mirror is approximately 12 microns by 12 microns, although other sizes may be made and employed in the present invention. Accordingly, depending upon the dispersing power of the prism and the prism to SLM spacing, a relatively narrow band of wavelengths will be focused onto each activatable portion of an SLM's active surfaces, such as a row of DMD mirrors.

Thus, a row of DMD mirrors aligned with the optical axis (of the prism) may be selectively activated (or deactivated) to cause the radiation incident upon the mirrors to bounce off the mirrors at an angle sufficient to cause the light to be passed to a focusing device, which is preferably parabolic focusing mirror. Other focusing devices, such as a lens, a system of lenses or optical fibers, may be employed in the SLM spectrometer of the present invention. Again the focusing device and SLM may be combined. In turn, the parabolic focusing mirror focuses the radiation from the activated (or deactivated) surface or row of mirrors onto a sensor or detector. This detector in turn measures the intensity or amount of energy in this particular wavelength or band of wavelengths. Any conventional spectrometer detectors may be employed in the SLM spectrometer of the present invention. Preferably, any detector employed is as linear as possible over as wide a wavelength range as possible, to provide a broadband spectrometer. However, known non-linear portions of a detector may be compensated for by post-detection software.

Accordingly, by selectively activating (or deactivating) each row of cells across the face of the SLM, it is possible to measure the presence or absence of energy at particular wavelengths, corresponding to the wavelengths incident upon the cell array. In this manner it is possible to generate a spectrum of wavelengths and the energy associated with those wavelengths. Again, the SLM of the present invention may be, for example, but not limited to, a deformable mirror device (DMD), a liquid crystal device (LCD), or a magneto-optic modulator, and may employ a linear or area array of such types of devices.

The DMD is uniquely suited to this because of the very small size of the DMD mirrors. It is possible to select a very small portion of the radiation spectrum for intensity measurement by the detector. Currently available DMDs have at least 512 by 512 arrays of micromirrors. Thus, the wavelength spectrum may be divided into at least 512 "bands" of wavelengths. In addition, a linear DMD having about 3.5 inches of active mirrors is also commercially available. By increasing or decreasing the "number" of active surface areas on an SLM (for a given wavelength spectrum and spacing), it is possible to increase or decrease the resolution of the spectrometer of the present invention. The resolution may thus be easily selected for specific applications or uses of the spectrometer.

However, as noted earlier herein, it is also possible to select the wavelength resolution of the spectrometer by appropriate selection of the dispersing power of the dispersing element and the spacing between the dispersing element and the SLM. In addition, to increase resolution, higher orders of spectra from the dispersing element may be employed as the radiation spectra supplied to the SLM. Proper selection of these variables may be made after the use of spectrometer (i.e. wavelength range and resolution desired) is known.

It is further contemplated by the present invention to couple the activation (or deactivation) of each of the rows of mirrors with a microprocessor (or processor) and to have the output of the sensor and/or detector digitized (preferably after amplification) by digitizer 31 and provided to the microprocessor. In this manner, a digital spectrometer is provided such that the microprocessor controls and analyzes the energy level at the various wavelengths and provides as an output a wavelength spectrum corresponding to that measured by the detector. The microprocessor may also expose the detector to the desired wavelength for a fixed but adjustable period of time, depending upon the intensity of the radiation, to provide an appropriate signal-to-noise ratio.

Existing commercial and laboratory spectrometers use a relatively large rotating mirror (which vibrates mechanically) to sweep the spectrum wavelengths across the sensor. The deformable mirror device, as the preferred SLM of the present invention, selects, with a very small mirror, the wavelength or band of wavelengths to be presented to the sensor. In this manner the SLM spectrometer of the present invention does not require any mechanical motion of the dispersing element to select the frequency to be scanned by the detector. More particularly, the SLM spectrometer of the present invention only has the electrical or mechanical movement of the activated (or deactivated) surface or cell of the SLM, which are preferably the micromirrors on the DMD. Thus, the SLM spectrometer of the present invention does not require motor driven mirrors or prisms with bearing surfaces which wear and change the calibration of the spectrometer. In addition, the SLM spectrometer of the present invention is not sensitive to such mechanical vibration, since the dispersing element and SLM are fixed. Accordingly, the SLM spectrometer of the present invention is more sensitive (i.e., of higher resolution) and more rugged than conventional spectrometers that employ motor driven rotating mirrors, prisms, or gratings.

In addition, calibration of the SLM spectrometer of the present invention is performed by a fixed alignment of the various components. Other spectrometers require that moving parts be timed and/or tracked to know what wavelength (or frequency) is being measured. The SLM spectrometer of the present invention does not require periodic alignment of the spectrometer based upon such timing circuitry. It also has the capability to have its adjustments "locked-in" to reduce any chance of misalignment due to vibrations. Additionally, the spectrometer is not required to be recalibrated due to the wear of moving parts. That is, the SLM spectrometer of the present invention may be calibrated, locked in place, and sealed.

As is well known in the art, various materials may be identified by the frequencies of the visible and near visible light that they absorb. The composition of complex materials may be predicted by comparing the spectra from known samples to the spectra of unknown samples. Nondestructive analysis of the composition of materials may be performed using a spectrometer of the present invention which is capable of measuring visible and near visible light.

The data from a digital spectrometer of the present invention may be employed as an input by a process control computer and the composition of the material predicted and controlled based upon this input.

Spectrum analyzers employing the concepts of the present invention may be implemented for any frequency range which is reflected or transmitted by the selected SLM device and for which a suitable sensor may be employed.

In addition, post-detection software in a processor associated with the spectrometer or a separate processor may employ specialized software to analyze the detected intensities versus wavelength. Such software may be so-called Hadamard software, which determines the wavelength content from various half-intensity measurements. That is half of the SLM is "activated" and supplies radiation to the detector, then the other half is activated. Then combinations of two quarters are activated, then combinations of four eights, and so on. Software may also be employed to compensate for known non-linear responses from the detector.

The SLM spectrometer of the present invention may be employed as a colorometer, with or without a processor and post-detection software. Colorometers are used to monitor the color of food products to ensure a uniform color for the consumer. Post-detection software may also be employed to convert any detected spectra into spectra corresponding to that seen by the human eye.

An infrared SLM spectrometer of the present invention may be particularly useful for detection of water content in various substances or compounds. For IR applications, the active surface of any reflective SLM device may need to be increased slightly to compensate for the longer IR wavelengths.

Figure 4:
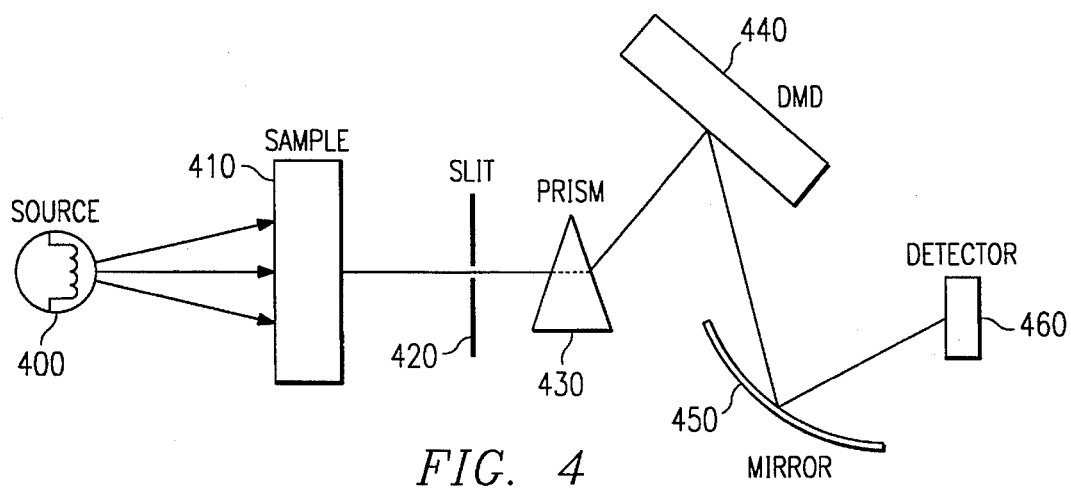
FIG. 4 depicts a general arrangement of the components of an SLM spectrometer of the present invention arranged for a transmissive analysis of a sample.

Referring now to FIG. 4 there may be seen a general arrangement of an SLM spectrometer of the present invention employed to analyze a sample in a transmissive mode. More particularly, it may be seen that there is a broad band wavelength lamp 400 which emits a known wavelength spectra of known intensity which passes through the sample 410 to be analyzed. Such lamps 400 are commercially available and are typically incandescent lamps containing a particular gas or mixture of gases. The radiation emanating from the sample 410 is then focused by an entrance slit 420 of the SLM spectrometer of the present invention onto the prism 430 after which it is analyzed in the manner described earlier herein.

Figure 5:
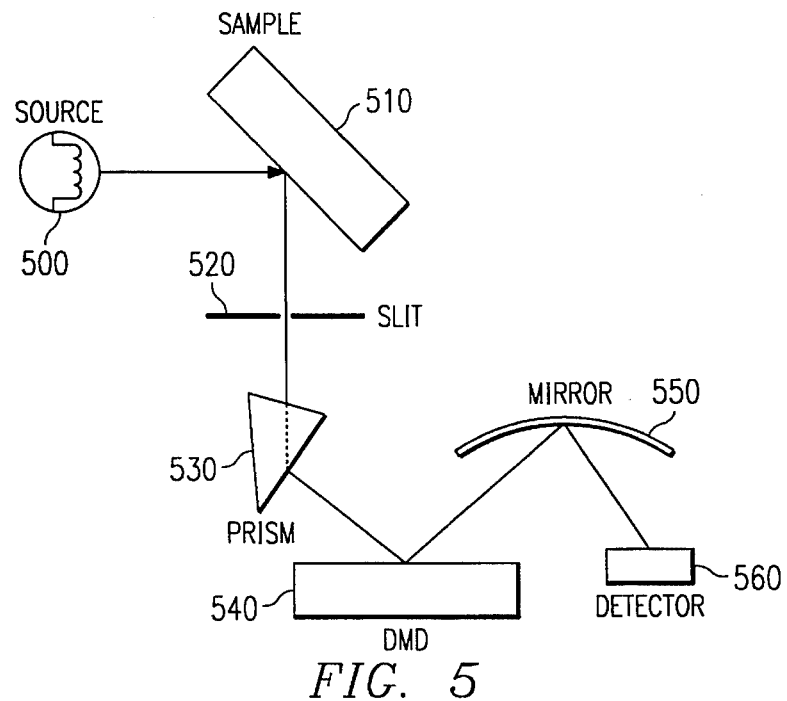
FIG. 5 depicts a general arrangement of the components of an SLM spectrometer of the present invention arranged for a reflective analysis of a sample.

Referring now to FIG. 5 there may be seen a general arrangement of an SLM spectrometer of the present invention employed to analyze a sample in a reflective mode. More particularly, it may be seen that there is again a lamp 500 providing a known broad band spectrum of known intensity which is reflected from a sample 510. The radiation reflected from the sample 510 is then focused by an entrance slit 520 onto the SLM spectrometer of the present invention where it is analyzed as described hereinbefore.

Many other variations and modifications may be made in the apparatus and techniques hereinbefore described, by those having experience in this technology, without departing from the concept of the present invention. Accordingly, it should be clearly understood that the apparatus depicted in the accompanying drawings and referred to in the foregoing description are illustrative only and are not intended as limitations on the scope of the invention.

What is claimed is:

1. A spectrometer comprising:

a collimator for collimating incident radiation;

a dispersing element for spectrally dispersing said collimated incident radiation into at least two portions of radiation;

at least two pairs of optical fiber, each said pair of optical fibers comprised of an input optical fiber and an output optical fiber, each said input optical fiber receiving one of said portions of radiation and transmitting said portion of radiation to said output optical fiber;

an optical switch associated with each said pair of optical fibers, each said optical switch for selectively enabling the transmission of said portion of radiation from said input optical fiber to said output optical fiber; and a detector for receiving said portion of radiant from said output optical fibers and for sensing the intensity of said portion of radiation.

2. The spectrometer of claim 1 wherein said output fibers are twisted thereby focusing said portions of radiation from said output fibers onto said detector.

3. The spectrometer of claim 1 further comprising:

a parabolic mirror between said output fibers and said detector for focusing said portions of radiation from said output fibers onto said detector.

4. The spectrometer of claim 1 further comprising:

a lens between said output fibers and said detector for focusing said portions of radiation from said output fibers onto said detector.

5. The spectrometer of claim 1 wherein said input optical fibers receive a higher order portion of radiation.

6. The spectrometer of claim 1 wherein said optical switch is a deformable mirror device.

7. The spectrometer of claim 1 wherein said optical switch is a liquid crystal device.

8. A spectrometer comprising:

a collimator for collimating incident radiation;

a dispersing element for spectrally dispersing said collimated incident radiation into at least two portions of radiation;

at least two pairs of optical fibers, each said pair of optical fibers comprised of an input optical fiber and an output optical fiber, each said input optical fiber receiving one of said portions of radiation and transmitting said portion of radiation to said output optical fiber;

a deformable micromirror device associated with each said pair of optical fibers, each said deformable micromirror device for selectively enabling the transmission of said portion of radiation from said input optical fiber to said output optical fiber; and a detector for receiving said portion of radiant from said output optical fibers and for sensing the intensity of said portion of radiation.

9. The spectrometer of claim 8 wherein said output fibers are twisted thereby focusing said portions of radiation from said output fibers onto said detector.

10. The spectrometer of claim 8 further comprising:

a parabolic mirror between said output fibers and said detector for focusing said portions of radiation from said output fibers onto said detector.

11. The spectrometer of claim 8 further comprising:

a lens between said output fibers and said detector for focusing said portions of radiation from said output fibers onto said detector.

12. The spectrometer of claim 8 wherein said input optical fibers receive a higher order portion of radiation.

* * * * *